(12) United States Patent
Lurie

(10) Patent No.: US 6,486,206 B1
(45) Date of Patent: Nov. 26, 2002

(54) MECHANICAL AND PHARMACOLOGIC THERAPIES TO TREAT CARDIAC ARREST

(75) Inventor: Keith G. Lurie, Minneapolis, MN (US)

(73) Assignee: CPRx Inc., Minneapolis, MN (US)

(*) Notice: Subject to any disclaimer, the term of this patent is extended or adjusted under 35 U.S.C. 154(b) by 0 days.

(21) Appl. No.: 09/538,432

(22) Filed: Mar. 29, 2000

Related U.S. Application Data

(63) Continuation of application No. PCT/US98/20461, filed on Sep. 29, 1998.
(60) Provisional application No. 60/088,362, filed on Sep. 29, 1997.

(51) Int. Cl.⁷ ............................................. A61K 31/195
(52) U.S. Cl. ....................... 514/561; 514/653
(58) Field of Search .................. 514/561, 653

(56) References Cited

U.S. PATENT DOCUMENTS 5,334,706 A * 8/1994 Pyzybelski ................. 530/385
5,588,422 A    12/1996 Lurie et al. ............ 128/200.24

OTHER PUBLICATIONS

Cohen, T.J., et al., "Active Compression–Decompression", *The Journal of the American Medical Association*, 267 (21), pp. 2916–2923, (Jun. 3, 1992).

Eisenberg, M.S., et al., "Long–Term Survival After Out–of–Hospital Cardiac Arrest", *The New England Journal of Medicine*, 306 (13), pp. 1340–1343, (Apr. 1, 1982).

Lindner, K.H., et al., "Effects of Active Compression–Decompression Resuscitation on Myocardial and Cerebral Blood Flow in Pigs", *Circulation*, 88 (3), pp. 1254–1263, (Sep. 1993).

Lurie, K.G., "Active compression–decompression CPR: a progress report", *Resuscitation*, 28 (2), pp. 115–122, (Oct. 1994).

Niemann, J.F., "Cardiopulmonary Resuscitation", *The New England Journal of Medicine*, 327 (15), pp. 1075–1080, (Oct. 8, 1992).

Sack, J.B., et al., "Survival From In–Hospital Cardiac Arrest With Interposed Abdominal Counterpulsation During Cardiopulmonary Resuscitation", *The Journal of the American Medical Association*, 267 (3), pp. 379–385, (Jan. 15, 1992).

Stiell, I.G., et al., "High–Dose Epinephrine in Adult Cardiac Arrest", *The New England Journal of Medicine*, 327 (15), pp. 1045–1050, (Oct. 8, 1992).

Woodhouse, S.P., et al., "High dose and standard dose adrenaline do not alter survival, compared with placebo, in cardiac arrest", *Resuscitation*, 30 (3), pp. 243–249, (Dec. 1995).

* cited by examiner

Primary Examiner—Zohreh Fay
(74) Attorney, Agent, or Firm—Schwegman, Lundberg, Woessner & Kluth, P.A.

(57) ABSTRACT

A method for resuscitating a patient from cardiac arrest, comprising: (a) administering CPR, and (b) administering: i) an amount of one or more vasopressor agents, or one or more vasopressinergic agonists, or a combination thereof, sufficient to increase the patient's arterial blood pressure; and ii) an amount of L-arginine, nitric oxide, a direct nitric oxide donor, or another nitric oxide donor, or a combination thereof, sufficient to enhance arterial blood flow to the patient's brain and heart, as well as kits and pharmaceutical compositions useful for practicing the method are described.

28 Claims, 4 Drawing Sheets

MECHANICAL AND PHARMACOLOGIC THERAPIES TO TREAT CARDIAC ARREST

PRIORITY OF INVENTION

This application is a Continuation of International Patent Application No. PCT/US98/20461, filed on Sep. 29, 1998, which claims priority under 35 U.S.C. §119(e) from U.S. Provisional Application 60/088,362, filed Sep. 29, 1997.

BACKGROUND OF THE INVENTION

In the United States each year, more than 350,000 people die from cardiac arrest prior to arriving in the hospital. Even when patients are resuscitated initially, more than half die in the hospital within the first 24 hours. Eisenberg et al., *NEJM* 306, 1340 (1982). Despite more than three decades of the practice of manual external chest compression or standard cardiopulmonary resuscitation "standard CPR", together with epinephrine administration, less than 5% of patients who suffer a cardiac arrest survive. Niemann, *NEJM,* 327, 1075 (1992). Though time to initiation of standard CPR is a critical factor in determining outcome, the inherent limitations of manual external chest compression are perhaps an even greater reason for the poor survival statistics. In light of the tremendous amount of time, money and energy involved in basic CPR performance and training, these statistics become even more disheartening. Although pharmacologic therapy, specifically intravenous epinephrine and antiarrhythmic therapies, have served to improve outcomes in some patients, the role of vasopressor agents during CPR remains controversial. Stiell et al., *NEJM,* 327, 1045 (1992).

Over the past 35 years since standard manual external chest compression was described, there have been a number of advances in the mechanical means available to improve overall cardiopulmonary resuscitation ("CPR") efficacy. Based on the assumption that increases in intrathoracic pressures will increase cardiac output during ventricular fibrillation, techniques such as the circumferential vest and active compression and decompression (ACD CPR) have been developed. Lurie, *Resuscitation,* 28, 115 (1994). In an effort to enhance filling of the coronary arteries and enhance venous return during the diastolic or decompression phase of CPR, techniques such as interposed abdominal counterpulsion CPR and use of a rapidly inflating and deflating intra-aortic balloon pump, as well as ACD CPR have been used. Sack et al., *JAMA,* 267, 379 (1992).

In addition to the research conducted on mechanical means to improve the efficacy of CPR, there has been a renewed interest in developing pharmacological therapies to improve the vital organ blood flow and overall survival of patients who have suffered a cardiac arrest. Such therapies typically include the intravenous administration of epinephrine during the performance of CPR. Epinephrine is an arterial constrictor, and its use is intended to enhance patient blood pressure during the resuscitation process. Even with epinephrine, however, survival after cardiac arrest is poor. Furthermore, recent studies have demonstrated no added benefit from doses of epinephrine higher than the traditional dose. Stiell et al., cited supra. Other recent studies also show no benefit of high or low dose epinephrine with placebo. (Woodhouse et al., *Resuscitation,* 30, 243 (1995).

U.S. Pat. No. 5,588,422, issued Dec. 31, 1996, discloses a method for resuscitating a patient from cardiac arrest, comprising actively inducing venous blood transport into the heart and arterial blood transport from the heart; ventilating the patient's lungs; administering to the patient concurrently with said inducing and ventilating steps an arterial constrictor (epinephrine) sufficient to increase the patient's arterial blood pressure, and an amount of a venodilator (nitroglycerin) sufficient to enhance arterial blood flow to the patient's brain and heart.

However, a continuing need exists for improved methods and pharmaceutical compositions for use during CPR, which result in enhanced long term survival among at least certain populations of cardiac arrest patients. Such methods and compositions would preferably enhance blood circulation and delivery of oxygenated blood to patient tissue, particularly heart and/or brain tissue, without significantly lessening patient blood pressure.

SUMMARY OF THE INVENTION

Surprisingly, it has been found that the administration of L-arginine (which is known to be a substrate for nitric oxide synthase) in combination with the vasopressor epinephrine leads to superior vital organ blood flow during CPR when compared with conventional epinephrine therapy, or with the administration of epinephrine or epinephrine and vasopressin, in combination with nitroglycerin. An increase in both the total myocardial blood flow and the endocardial to epicardial perfusion ratio result. Thus, the present invention provides a method for resuscitating a patient from cardiac arrest, comprising: (a) administering CPR, and (b) administering: i) an amount of one or more vasopressor agents, or one or more vasopressinergic agonists, or a combination thereof, sufficient to increase the patient's arterial blood pressure; and ii) an amount of L-arginine, nitric oxide, or a direct nitric oxide donor, or a combination thereof, sufficient to enhance arterial blood flow to the patient's brain and heart.

The invention also provides a kit for the treatment of cardiac arrest comprising packaging material containing: a) an amount of one or more vasopressor agents, or one or more vasopressinergic agonists, or a combination thereof, sufficient to increase a patient's arterial blood pressure; b) an amount of L-arginine, nitric oxide, or a direct nitric oxide donor, or a combination thereof, sufficient to enhance arterial blood flow to a patient's brain and heart; and c) instruction means indicating that the compounds described in a) and b) are to be administered to a patient undergoing cardiopulmonary resuscitation.

The invention also provides a pharmaceutical composition comprising: a) an amount of one or more vasopressor agents, or one or more vasopressinergic agonists, or a combination thereof, sufficient to increase arterial blood pressure; b) an amount of L-arginine, nitric oxide, or a nitric oxide donor, or a combination thereof, sufficient to enhance arterial blood flow to the brain and heart; and c) a pharmaceutically acceptable carrier.

The invention also provides the use of a combination of: a) an amount of one or more vasopressor agents, or one or more vasopressinergic agonists, or a combination thereof, sufficient to increase a patient's arterial blood pressure; and b) an amount of L-arginine, nitric oxide or a direct nitric oxide donor, or a combination thereof, sufficient to enhance arterial blood flow to a patient's brain and heart; to prepare a medicament useful for enhansing the survival of a cardiac arrest patient.

DETAILED DESCRIPTION OF THE INVENTION

Figure 1:
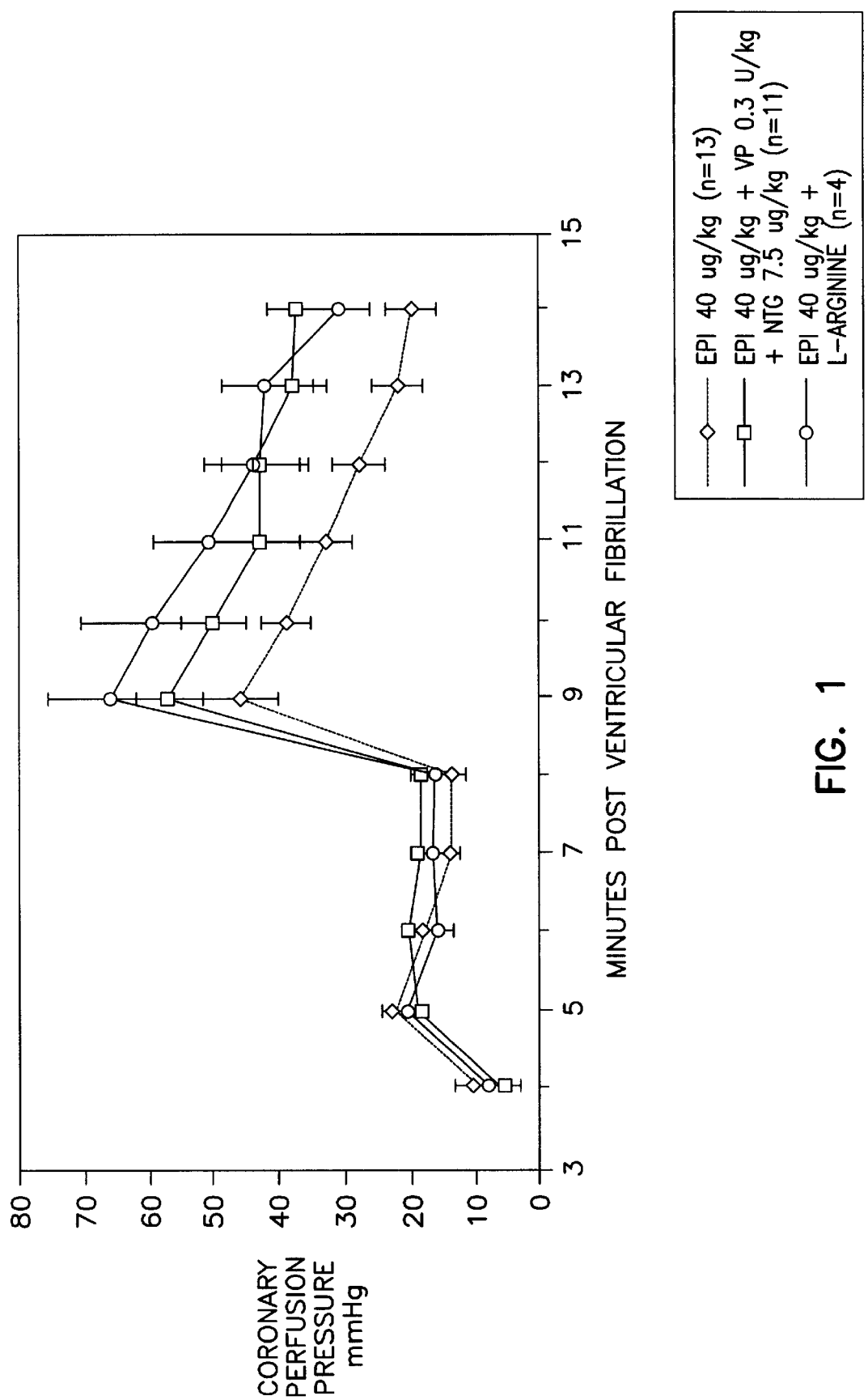
FIG. 1 illustrates the coronary perfusion pressures (CPP) (diastolic aortic minus right arterial pressures) of pigs (n=4 per group) resuscitated from ventricular fibrillation with epinephrine (EPI) alone 40 µg/kg; epinephrine 40 µg/kg, vasopressin (VP) 0.3 U/kg and nitroglycerin (NTG) 7.5 µg/kg; or epinephrine 40 µg/kg and L-arginine 20 mg/kg.
Figure 2A:
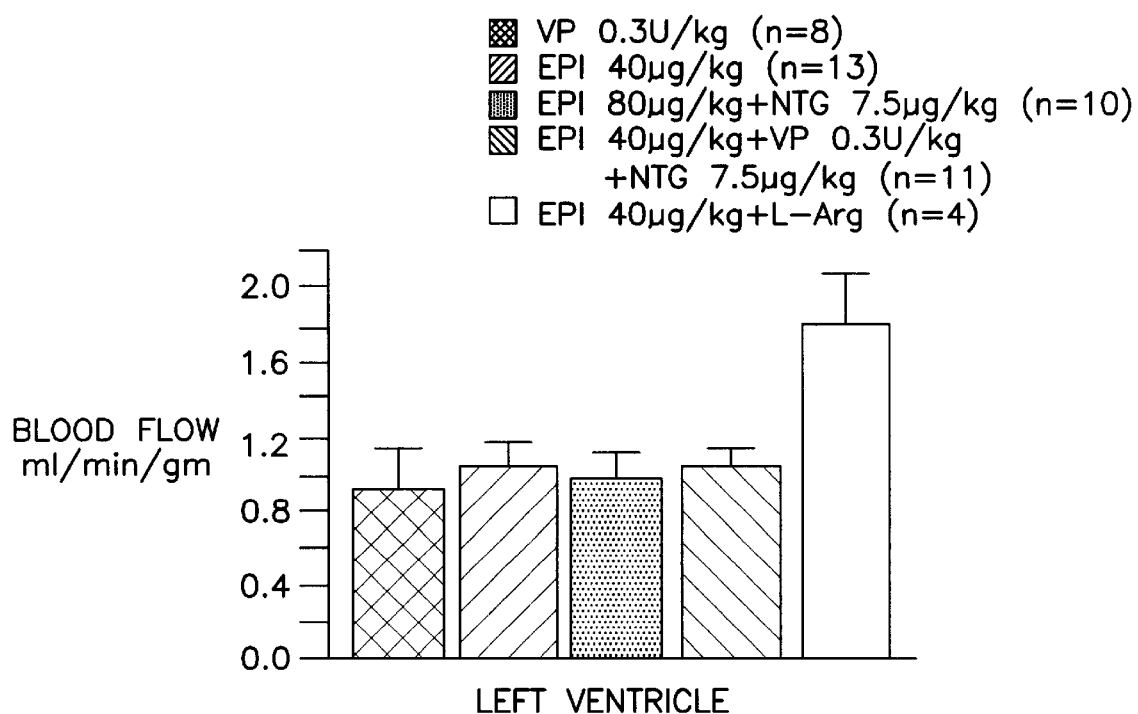
FIG. 2 illustrates vital organ blood flow assessed after four minutes of ventricular fibrillation, four minutes of standard CPR, and two minutes after drug administration, with vasopressin (VP) 0.3 U/kg; epinephrine (EPI) 40 µg/kg; epinephrine 80 µg/kg and nitroglycerin (NTG) 7.5 µg/kg; epinephrine 40 µg/kg, vasopressin (VP) 0.3 U/kg and nitroglycerin (NTG) 7.5 µg/kg; and epinephrine 40 µg/kg and L-arginine 20 mg/kg.
Figure 2B:
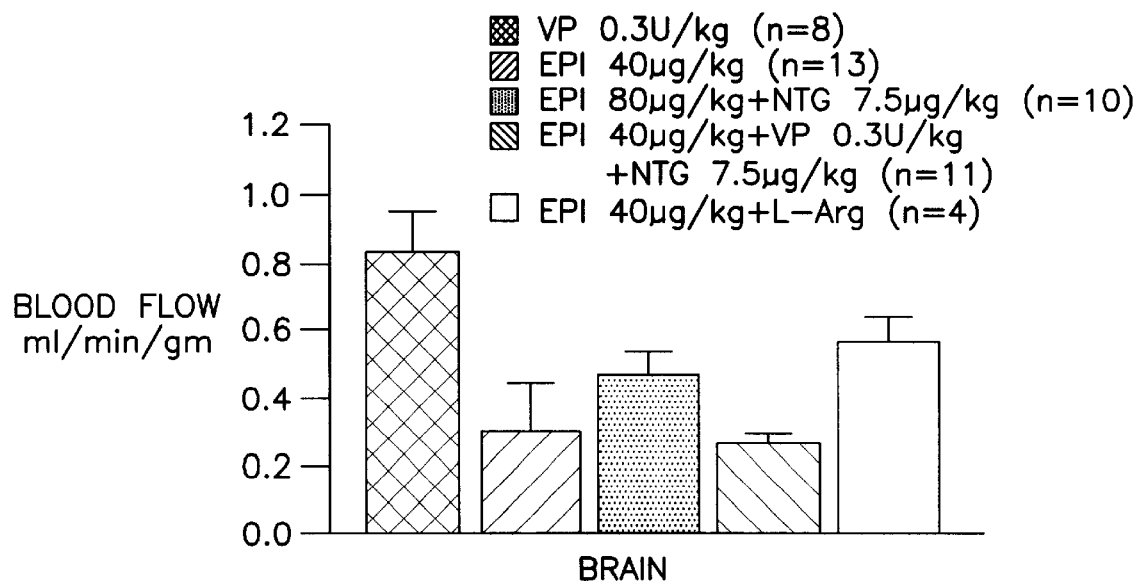

Cardiac arrest generally refers to conditions comprising the loss of effective heart function and the loss of effective blood circulation. Specific conditions treatable by the present invention include ventricular fibrillation, characterized by rapid contractions and twitching of the heart muscle; asystole, characterized by the substantial absence of contractions of the heart; and pulseless electrical activity (PEA) or electromechanical dissociation (EMD), characterized by the persistence of electrical activity in the heart without associated mechanical contractions.

Methods of Cardiopulmonary Resuscitation (CPR)

As used herein, the term cardiopulmonary resuscitation ("CPR") includes all forms of cardiopulmonary resuscitation, for example, standard cardiopulmonary resuscitation, cardiopulmonary resuscitation using a circumferential vest, active compression and decompression cardiopulmonary resuscitation (ACD CPR), interposed abdominal counterpulsation (IAC) cardiopulmonary resuscitation, cardiopulmonary resuscitation using a rapidly inflating and deflating intra-aortic balloon pump, as well as open chest cardiopulmonary resuscitation, or combinations thereof.

CPR involves the active inducement of blood transport to the heart and out of the heart. It includes both the transport of venous blood from the extremities and abdomen, into the thorax and heart, as well as the transport of blood from the heart into the lungs and arterial system. Both induced blood transport and lung ventilation are preferably achieved by certain advanced cardiopulmonary resuscitation methods, such as ACD CPR, as described in Cohen et al., *JAMA*, 267, 2916 (1992), and IAC, as described in Neimen, *N. Engl. J. Med.*, 327, 1075 (1992). Induced blood transport and lung ventilation can be achieved, but to a lesser extent, with standard chest massage and CPR techniques. Optionally, additional measures may be taken to provide lung ventilation, such as use of an endotracheal tube, mouth-to-mouth resuscitation, or the like.

Pharmacologic Agents

1. Vasopressors

The term vasopressors includes adrenergic agonists (direct-acting sympathomimetics), that may increase heart rate, increase blood pressure, increase vital organ perfusion, enhance atrioventricular conduction, and increase strength of the heart contraction (positive inotropic action). Adrenergic agonists also may induce lipolysis and thus increase the concentration of plasma free fatty acids. These effects may be achieved, in part, through the activation of the adenyl cyclase system and the intermediation of 3', 5'-cyclic adenosine monophosphate (cyclic AMP). Adrenergic agonists suitable for use in the present invention include, but are not limited to, epinephrine, norepinephrine, dopamine, dobutamine, isoproterenol, phenylephrine, methoxamine, and the like. Preferably, the adrenergic agonist has some $\alpha_1$ receptor activity. A preferred adrenergic agonist is epinephrine.

Administration of more than one adrenergic agent, for example epinephrine and isoprotemol, may also provide the desired therapeutic effect. Thus, adrenergic agents with relatively great α and/or β adrenoceptor selectivity may be administered in combination according to the invention.

2. Vasopressinergic Agonists

The term vasopressinergic agonists includes compounds with vasopressin, receptor agonist activity, for example, vasopressin. Other suitable vasopressinergic agonists include vasopressin, selective agonists such as [Phe$^2$, Orn$^8$]-oxytocin. A preferred vasopressinergic agonist is vasopressin.

3. L-Arginine

L-Arginine is the main substrate for nitric oxide synthase and it causes the elevation of nitric oxide levels when administered to the body. It is to be understood that the methods of the invention also allow for the administration derivatives of L-arginine (for example lower alkyl esters and amides formed from the carboxy or amino functionalities of L-arginine) provided such derivatives cause the elevation of nitric oxide levels when administered in vivo.

L-Arginine is converted by nitric oxide synthase to nitric oxide and L-citrulline. In the vasculature, nitric oxide is thought to diffuse to the vascular smooth muscle to produce vasodilation R. A. Busse, et al., *Circulation*, 1993, 86, V18–125; and S. Moncada, et al., *Cardiovascular Pharm*, 1991,17 Suppl.3:S1–S9). Additionally, nitric oxide released by the endothelium causes vascular relaxation and in that manner can increase blood flow to organs subserved by nitric oxide sensitive arteries.

4. Nitric Oxide

Because L-arginine, when administered in the course of practicing the methods of the invention, is believed to act, at least in part, by elevating nitric oxide levels in vivo, the administration of nitric oxide itself may be substituted for the administration of L-arginine in the method of the invention.

5. Direct Nitric Oxide Donor

The term "direct nitric oxide donor" as used herein means compounds that are capable of directly delivering NO to vascular smooth muscle, without requiring enzymatic activation of a prodrug. The term does not include nitroglycerine. Such compounds are known to the art, and include DEA/NO ($Et_2N[N_2O_2]Na$), PAPA/NO ($CH_3(CH_2)_2N[N_2O_2]^-(CH_3)NH_3^+$), SPER/NO ($H_2N(CH_2)_3NH_2^+(CH_2)_4N[N_2O_2]^-(CH_2)_3NH_3^+$), DPTA/NO ($H_2N(CH_2)_3N[N_2O_2]^-(CH_2)_3NH_3^+$), and DETA/NO ($H_2N(CH_2)_2N[N_2O_2]^-(CH_2)_2NH_3^+$). For example, see J. G. Diodati, et al. Complexes of Nitric Oxide with Nucleophiles as Agents for the Controlled Biological Release of Nitric Oxide: Hemodynamic Effect in the Rabbit," *Journal of Cardiovascular Pharmacology*, 1993, 22, 287–292; and D. L. Mooradian, et al. "Nitric Oxide (NO) Donor Molecules: Effect of NO Release Rate on Vascular Smooth Muscle Cell Prolieration In Vitro," *Journal of Cardiovascular Pharmacology*, 1995, 25, 674–678. Such direct nitric oxide donors may be particularly useful to enhanse arterial blood flow to a patients brain and heart during CPR, because they do not requiring enzymatic activation to release nitric oxide. Thus, direct nitric oxide donors are particularly useful in the therapeutic compositions and methods of the invention. A preferred nitric oxide donor is DEA/NO or PAPA/NO.

Direct nitric oxide donors can conveniently be prepared by reacting nitric oxide with a nucleophyle, such as an amine (e.g. a primary or secondary amine). For Example, see C. M. Maragos, et al. "Complexes of NO with Nucleophyles as Agents for the Controlled Biological Release of Nitric Oxide. VasoRelaxant Effects" *J. Med. Chem.*, 1991, 34, 3242–3247; R. S. Drago "Reactions of Nitrogen(II) Oxide." In *Free Radicals in Inorganic Chemistry*: Advances in Chemistry Series, Number 36: American Chemical society: Washington D.C., 1962, pp 143–149; and T. J. Hansen, et al, "N-Nitrosation of Secondary Amines by Nitric Acid via the 'Drago Complex.' In *N-Nitroso Compounds, Occurance and Biological Effects*, IARC Scientific Publications No. 41, Inernational Agency for Research on Cancer: Lyon, 1982, pp21–29.

6. Other Nitric Oxide Donors

Any compound capable of increasing the amount of nitric oxide available to vascular smooth muscle, and thereby enhansing arterial blood flow to a patient's brain and heart during CPR, can be used in the methods and compositions of the invention. Agents that cause the endothelium to release nitric oxide include adenosine, acetylcholine, bradykinin, and substance P. Additionally, agents that donate nitric oxide, the so called nitrovasodilators such as nitroglycerine and sodium nitroprusside must undergo enzymatic metabolism before they can produce vascular relaxation through generation of nitric oxide (P. Seth, H. L. Fung, *Biochem Pharmacol*, 1993, 46, 1481–1486). Other useful nitrovasodilators include glyceryl trinitrate, S-nitroso-N-acylpenicillamine, S-nitrosoglutathione, and linsidomine. See R. J. MacAllister et al., "Relative Potency And Arteriovenous Selectivity of Nitrovasodilators on Human Blood Vessels: An Insight into the Targeting of Nitric Oxide Delivery," *The Journal of Pharmacology and Experimental Therapeutics*, 1995,273, 154–160. Preferably, the other nitric acid donor is not nitroglycerine.

Modes of Administration

The aforementioned pharmacologic agents (i.e., vasopressors, vasopressinergic agonists, L-arginine, nitric oxide, direct nitric oxide donors, and other nitric oxide donors) are preferably administered to the patient immediately before, concurrently with, or as soon as possible after, the initiation of CPR, preferably being administered within from 0 to 60 minutes after such initiation, more preferably being administered from 0 to 10 minutes after such initiation. Therefore, steps (a) and (b) in claim 1 can be carried out simultaneously, or in any order. Both the initiation of CPR and the administration of the combination of active ingredients should be initiated as shortly as possible after the cardiac arrest, with drug administration preferably beginning within 10 minutes of arrest. Administration of the combination dose of pharmacologic agents can be repeated during procedures which last for more than 10 minutes, usually being repeated every 3 to 10 minutes.

The pharmacologic agents can be administered by any technique which assures rapid absorption into the patient's circulation, and preferably are administered parenterally, i.e., by injection or infusion, intravenously, endotracheally, sublingually, intracardiac, intraosseally, transdermally, or by other routes, including inhalation and insufflation. Intravenous injections will usually be made to a peripheral or central vein in a conventional manner. Endotracheal administration may also be performed and is particularly suitable if an endotracheal tube has been introduced in order to enhance lung ventilation, and intravenous access is not immediately available. Devices and methods suitable for endotracheal administration of pharmacologic agents according to the present invention are described in U.S. Pat. No. 4,693,243. In the case of endotracheal administration, the total dosages described above will generally be increased in order to offset the inefficiencies of such an administration route. The dosages will usually be increased from two-fold to three-fold.

The pharmacologic agents will preferably be administered together in a single dosage or bolus, but could also be administered separately and/or sequentially to the patient. Furthermore, the total desired dosage of each of the pharmacologic agents may be administered in two or more discrete boluses.

When nitric oxide is administered according to the invention, it may conveniently be administered to a patients lungs as a gas, under pressure, or as an aqueous solution.

Dosage Forms

The solid or liquid pharmacologic agents can be formulated for administration to a human patient in cardiac arrest in one or more unit dosage forms comprising an effective amount of the pharmacologic agent or agents, in combination with a pharmaceutically acceptable liquid carrier, such as distilled water, physiological salt solutions such as normal saline, buffers, and the like. Such dosage forms will typically include a pharmaceutically acceptable preservative, and may include other components commonly employed in solutions suitable for intravenous and/or endotracheal administration such as nontoxic surfactants.

Unit dosage forms comprising the active agents can be formulated so as to deliver single or multiple dosages of the pharmacologic agents parenterally, as by injection or infusion. Such dosage forms include prefilled bottles, ampules, plastic bags or preloaded syringes. Methods for preparing such pharmaceutical compositions and unit dosage forms are well known in the art and described in more detail in various sources including, for example, *Remington's Pharmaceutical Science*, 15th Edition, Mack Publishing, Easton, Pa. (1980).

Unit dosage forms suitable for injection or infusion can include sterile concentrated aqueous or aqueous-alcoholic solutions or dispersions which are adapted for extemporaneous dilution to yield sterile injectable or infusible solutions or dispersions. Preferably, the ultimate dosage form should be sterile, fluid and stable under the conditions of manufacture and storage. The liquid carrier or vehicle can be a solvent or liquid dispersion medium comprising, for example, a major portion of water in combination with ethanol, a polyol (for example, glycerol, propylene glycol, and liquid polyethylene glycols, and the like), vegetable oils, nontoxic glycerol esters, lipids (for example, dimyristoyl phosphatidyl choline) and suitable mixtures thereof. The proper fluidity can be maintained, for example, by the formation of liposomes, by the maintenance of the required particle size in the case of dispersion or by the use of nontoxic surfactants. The proper pH can be maintained with a variety of different buffers, for example, citrate or acetate. Sterile injectable or infusible solutions are prepared by incorporating the pharmacilogic agents in the required amount in the appropriate solvent with various of the other ingredients enumerated above, and as required, followed by filter sterilization.

Transdermal applications may require preparation of the unit dosage forms in suitable pastes, gels or the like, together with an effective carrier to promote either passive or active (electrophoretic) transport into the vasculature.

Dosages

The dosage of the pharmacologic agents can be varied widely, in accord with the size, age and condition of the patient. However, when administered according to the invention, it is preferred that: epinephrine, is administered in a dosage of from about 0.25 mg to 10 mg, preferably in a dosage of from about 0.75 mg to about 1.25 mg (i.e., total amount given to the patient at one time point during the procedure; administration may be repeated at successive time points as described below); vasopressin be administered in a dosage of from about 10 units to 120 units, preferably in a dosage of from about 10 units to about 60 units; L-arginine be administered in a dosage of about 1 to 50 mg/kg, preferably in a dosage of about 10 to 30 mg/kg; and direct nitric oxide donors be administered at a dose of about 0.5 to 500 nmol/kg, preferably at a dose of about 1 to 100 nmol/kg, and more preferably at a dose of about 1.5 to 10 nmol/kg.

Nitric Oxide can be administered as an inhalational agent (dose range about 0.01 to 500 ppm, preferably from 0.1 to 20 pm. D. N. Cornfield et al., *J. Lab Clin Med,* 1996, 127, 530–539. More preferably, nitric oxide can be administered as a saturated solution. In water, nitric oxide is soluable, with a mole fraction solubility of $3.69 \times 10^{-5}$ at room temperature. Nitric oxide-saturated saline solution can be prepared at a concentration of about 1.0 mmol/liter and administered at a dose range of about 0.01–3.0 μm nitric oxide/kg (J. W. Chambers et al., *Am. J. Physiol.,* 1996, 271, H1584–1593).

The above dosages represent approximate ranges and preferred ranges for adults, and would be reduced somewhat for administration to children and infants.

Kits

The invention also provides a kit that may facilitate practicing the methods of the invention. Accordingly, the invention provides, a kit for the treatment of cardiac arrest comprising packaging material containing: a) an amount of one or more vasopressor agents, or one or more vasopressinergic agonists, or a combination thereof, sufficient to increase a patient's arterial blood pressure; b) an amount of L-arginine, nitric oxide, a direct nitric oxide donor, or another nitric oxide donor, sufficient to enhance arterial blood flow to a patient's brain and heart; and c) instruction means indicating that the compounds described in a) and b) are to be administered to a patient undergoing cardiopulmonary resuscitation. The pharmacologic agents or unit dosage forms thereof may be packaged together or separately.

According to the invention, the packing material may additionally include one or more means for administering the pharmacologic agents, for example, a syringe or an endotracheal tube. Said means may preferably be a prefilled syringe comprising one or more of the pharmacologic agents, or unit dosage forms thereof.

Pharmaceutical Compositions

The invention also provides a pharmaceutical composition comprising: a) an amount of one or more vasopressor agents, or one or more vasopressinergic agonists, or a combination thereof, sufficient to increase a patient's arterial blood pressure; and b) an amount of L-arginine, nitric oxide, a direct nitric oxide donor, or an other nitric oxide donor, sufficient to enhance arterial blood flow to a patient's brain and heart; in combination with a pharmaceutically acceptable carrier.

Additional Agents

In addition to pharmacologic agents described above, the method may further comprise the administration of, and the kits or pharmaceutical compositions may include, other active substances which enhance the therapeutic effectiveness of the pharmacologic agents. For example, the methods may further comprise the administration of, and the kits or compositions may also include, mannitol in an amount effective to reduce swelling of the brain, heart, and/or kidneys, (inhibit edema) due to mannitol's osmotic properties. Mannitol may also enhance blood pressure. Mannitol may be administered at a dosage in the range from about 1 g to 100 g, preferably from about 5 g to 50 g.

A calcium channel blocker, such as diltiazem, verapamil, nifedipine, and the like, in an amount effective to inhibit calcium overload, may also optionally be administered when practicing the methods of the invention, or may be included in the kits described herein. Typically, a unit dosage form of diltiazem would comprise about 0.5 mg to 60 mg, preferably from about 0.5 mg to 20 mg. A unit dosage form of verapamil would comprise about 0.5 mg to 60 mg, preferably from about 0.5 mg to 5 mg. A unit dosage form of nifedipine would be present in a dosage from about 0.2 mg to 10 mg, preferably from about 0.5 mg to 5 mg.

Specific and Preferred Embodiments

The specific and preferred embodiments as well as the Examples and descriptions provided in the application are for illustration and they do not limit the invention in anyway.

In a specific embodiment the invention provides a method for resuscitating a patient from cardiac arrest, comprising: (a) administering cardiopulmonary resuscitation ("CPR"), and (b) administering: i) an amount of one or more vasopressor agents, or one or more vasopressinergic agonists, or a combination thereof, sufficient to increase the patient's arterial blood pressure; and ii) an amount of L-arginine or nitric oxide, sufficient to enhance arterial blood flow to the patient's brain and heart.

In another specific embodiment the invention provides a method for resuscitating a patient from cardiac arrest, comprising: (a) administering cardiopulmonary resuscitation ("CPR"), and (b) administering: i) an amount of one vasopressor agent, sufficient to increase the patient's arterial blood pressure, and ii) an amount of L-arginine, sufficient to enhance arterial blood flow to the patient's brain and heart. Preferably, the vasopressor agent is selected from the group consisting of epinephrine, dopamine, norepinephrine, isoproterenol, phenylephrine, dobutamine and methoxamine. More preferably, the vasopressor agent is epinephrine.

In another specific embodiment the invention provides a method for resuscitating a patient from cardiac arrest, comprising: (a) administering cardiopulmonary resuscitation ("CPR"), and (b) administering: i) an amount of a vasopressinergic agonist, sufficient to increase the patient's arterial blood pressure; and ii) an amount of L-arginine, sufficient to enhance arterial blood flow to the patient's brain and heart Preferably, the vasopressinergic agonist is vasopressin.

In another specific embodiment the invention provides a method for resuscitating a patient from cardiac arrest, comprising: (a) administering cardiopulmonary resuscitation ("CPR"), and (b) administering: i) an amount of a combination of one or more vasopressor agents and one or more vasopressinergic agonists, sufficient to increase the patient's arterial blood pressure, and ii) an amount of L-arginine, sufficient to enhance arterial blood flow to the patient's brain and heart. Preferably, the combination comprises a vasopressor agent selected from the group consisting of epinephrine, dopamine, norepinephrine, isoproterenol, phenylephrine, dobutamine and methoxamine. More preferably, the combination comprises epinephrine. Preferably, the the combination comprises the one vasopressinergic agonist vasopressin.

In another specific embodiment the invention provides a method for esuscitating a patient from cardiac arrest, comprising: (a) administering CPR, and b) administering an amount of: i) one or more vasopressor agents, or one or more vasopressinergic agonists, or a combination thereof; and ii) L-arginine, or nitric oxide, wherein said amount is sufficient to enhance arterial blood flow to the patient's brain and heart, or is sufficient to increase the patient's arterial blood pressure.

In another specific embodiment the invention provides a kit for the treatment of cardiac arrest comprising packaging material containing: a) an amount of one or more vasopressor agents, or one or more vasopressinergic agonists, or a combination thereof, sufficient to increase a patient's arterial blood pressure; b) an amount of L-arginine or nitric oxide, sufficient to enhance arterial blood flow to a patient's brain and heart; and c) instruction means indicating that the compounds described in a) and b) are to be administered to a patient undergoing cardiopulmonary resuscitation. Preferably, the kit contains: a) about 0.25 mg to 10 mg of epinephrine; b) about 50 mg to 5.0 g L-arginine; and c) instruction means indicating that the epinephrine and L-arginine are to be administered to a patient undergoing cardiopulmonary resuscitation.

In another specific embodiment the invention provides a pharmaceutical composition comprising: a) an amount of one or more vasopressor agents, or one or more vasopressinergic agonists, or a combination thereof, sufficient to increase a patient's arterial blood pressure; and b) an amount of L-arginine, sufficient to enhance arterial blood flow to a patient's brain and heart; in combination with a pharmaceutically acceptable carrier.

In another specific embodiment the invention provides a pharmaceutical composition comprising: a) an amount of epinephrine sufficient to increase a patient's arterial blood pressure; b) an amount of L-arginine, sufficient to enhance arterial blood flow to a patient's brain and heart; and c) a pharmaceutically acceptable carrier. Preferably, the composition comprises: a) about 0.25 mg to 10 mg of epinephrine; b) about 50 mg to 5.0 g L-arginine; and c) a pharmaceutically acceptable carrier.

In another specific embodiment the invention provides the use of a combination of: a) epinephrine; and b) L-arginine, nitric oxide, or a direct nitric oxide donor; to prepare a medicament useful for enhansing the survival of a cardiac arrest patient.

The invention will be further described by reference to the following detailed examples.

EXAMPLE 1

Materials and Methods

Healthy female domestic farm pigs (28–33 kgs) were fasted overnight and anesthetized with pentobarbital (20 mg/kg IV bolus followed by 2.5 mg/kg/hr IV infusion) via an ear vein. Once anesthetized, pigs were placed in the dorsal recumbent position and intubated using standard endotracheal intubation technique. They were ventilated during the preparatory phase of the experiment and after return of spontaneous circulation at the end of the experiment with a mechanical respirator (model 607, Harvard Apparatus Co., Inc., Dover, Mass.). The tidal volume was set at 450 cc and delivered between 11 and 15 breaths per minute with supplemental oxygen at 2 liters/minute. Normal saline solution was administered intravenously through the preparative and study periods using an infusion pump (Flo-Gard 6201, Baxter Healthcare, Deerfield, Ill.).

The preparatory phase, which includes cannulation of both femoral arteries and the right jugular vein, as well as calibration of all instruments, required approximately 2 hours. Once venous access was obtained, animals received normal saline solution at approximately 300–400 ml/hr to maintain diastolic right atrial pressures of 3–5 mm Hg. Arterial blood gases were analyzed every 30 minutes to insure adequate acid base status and oxygenation. Left ventricular and ascending aortic arch blood pressures were monitored using a single high fidelity micromanometer catheter (Millar, Houston, Tex.). This aorto-left ventricular catheter has a lumen for injecting radiolabeled microspheres and it was positioned, under fluoroscopic guidance, 15 minutes prior to initiation of VF. Right atrial pressures were monitored using a micromanometer catheter (Millar) inserted through a right jugular vein sheath. The micromanometer catheters were calibrated to atmospheric pressure immediately prior to inserting them into the pig.

A 5 French bipolar packing catheter (Daig, Inc., Minnetonka, Minn.), used to induce ventricular fibrillation (VF) with alternating current at 7 volts and 60 Hz, was inserted through a second right jugular vein sheath and positioned using fluoroscopy in the right ventricular apex. For withdrawal of reference blood samples to measure organ blood flow, a 7F catheter was advanced by femoral arterial access to the aortic arch. Body temperature was monitored continuously via a rectal probe (Yellow Springs Instrument Co., Yellow Springs, Ohio). Core temperatures were maintained between 36.5 and 38.5° C. using a heating pad. Five minutes prior to induction of VF, 5000 U of sodium heparin was administered intravenously.

Experimental

The effect of an L-arginine/epinephrine drug combination was studied in a porcine model of ventricular fibrillation using standard CPR. In this protocol, in which the materials and methods were as described above, an automated device was used to apply standard CPR. Lindner et al., *Circulation*, 88, 1254 (1993). Radiolabeled microspheres were used to measure myocardial blood flows during ventricular fibrillation prior to drug therapy and 2 minutes after drug administration.

With 4 pigs/group, using the protocol described hereinabove, the coronary perfusion pressures (CPP) (diastolic aortic minus right arterial pressures) were measured. Results are illustrated in FIG. 1. Unexpectedly, it was discovered that the administration of L-arginine in combination with epinephrine, using a relatively low dose of epinephrine (40 $\mu$g/kg) and a relatively high dose of L-arginine (20 mg/kg), gives a marked and abrupt increase in coronary perfusion pressure, with peak diastolic coronary perfusion pressures found to be as high or higher than those observed with the best "balanced" triple therapy of epinephrine (40 $\mu$g/kg), vasopressin (0.3 U/kg) and nitroglycerin (7.5 $\mu$g/kg). The administration of L-arginine and epinephrine also gives peak diastolic coronary perfusion pressures higher than those observed with epinephrine (80 $\mu$g/kg) and nitroglycerin (7.5 $\mu$g/kg).

Vital organ blood flow was also assessed after four minutes of ventricular fibrulation, four minutes of standard CPR, and two minutes after drug administration. The administration of epinephrine (40 $\mu$g/kg) and L-arginine (20 mg/kg) provides left ventricle blood flow that is superior to the blood flow obtained by administering vasopressin (VP) (0.3 U/kg) alone; epinephrine (EPI) (40 $\mu$g/kg) alone; epinephrine (80 $\mu$g/kg) in combination with nitroglycerin (NTG) (7.5 µg/kg); or epinephrine (40 µg/kg), in combination with vasopressin (0.3 U/kg) and nitroglycerin (7.5 µg/kg). The administration of epinephrine and L-arginine also provides blood flow to the brain that is superior to the blood flow obtained by administering epinephrine (40 µg/kg) alone; epinephrine (80 µg/kg) in combination with nitroglycerin (7.5 µg/kg); or epinephrine (40 µg/kg), in combination with vasopressin (0.3 U/kg) and nitroglycerin (7.5 µg/kg). The administration of L-arginine in combination with epinephrine increases blood flow to the endocardium significantly more than epinephrine alone. The mean±SEM endocardial:epicardial ratio was 1.37±0.29 with L-arginine/epinephrine, and was 0.81±0.21 with epinephrine alone.

EXAMPLE 2

Figure 3:
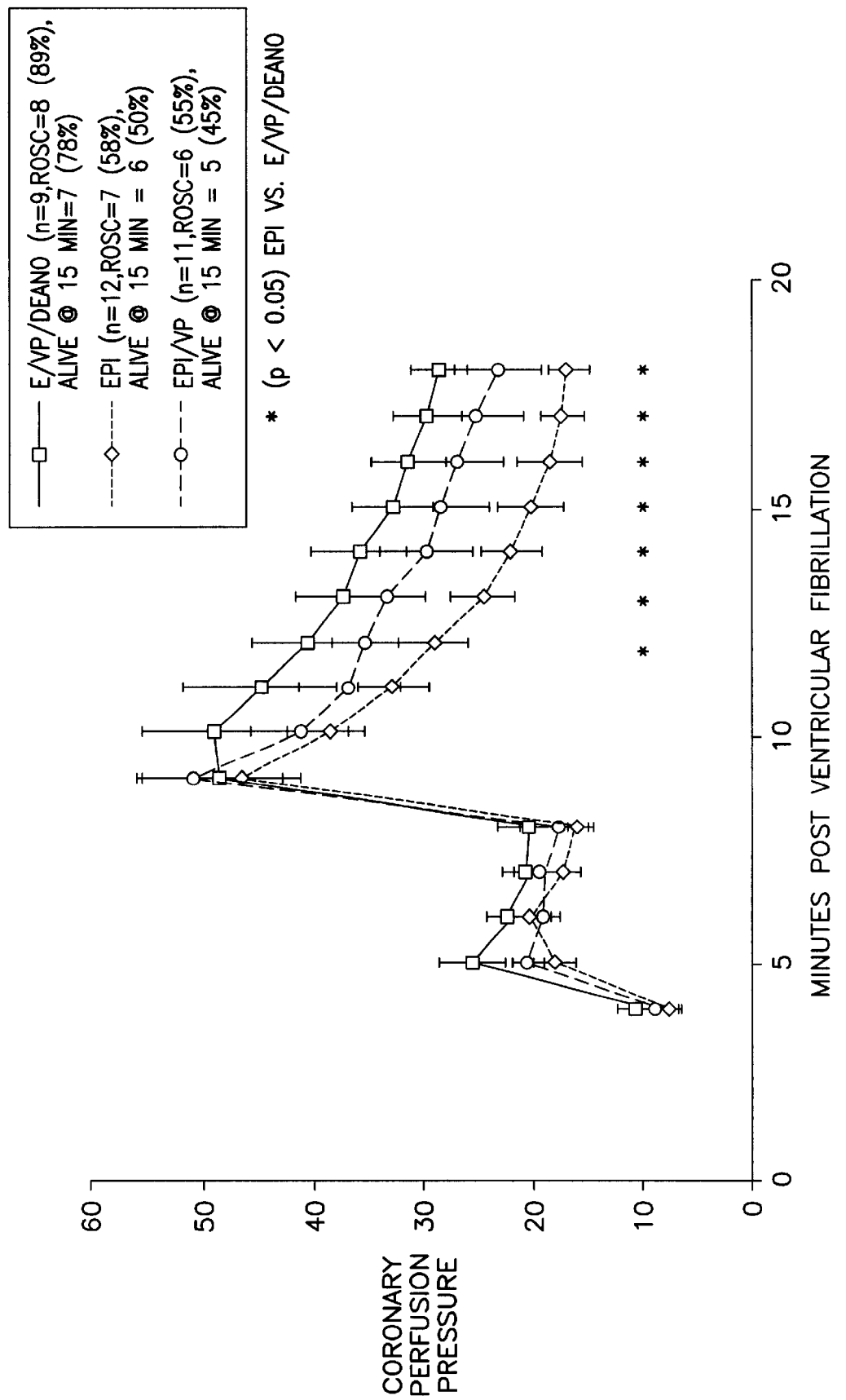
FIG. 3 illustrates the coronary perfusion pressures (CPP) (diastolic aortic minus right arterial pressures) of pigs (n≧9 per group) resuscitated from ventricular fibrillation with epinephrine (EPI) alone 40 µg/kg; epinephrine 40 µg/kg and vasopressin (VP) 0.3 U/kg; and epinephrine 40 µg/kg, vasopressin (VP) 0.3 U/kg and DEA/NO 0.14 µg/kg; ROSC=return of spontaneous circulation.
Figure 4:
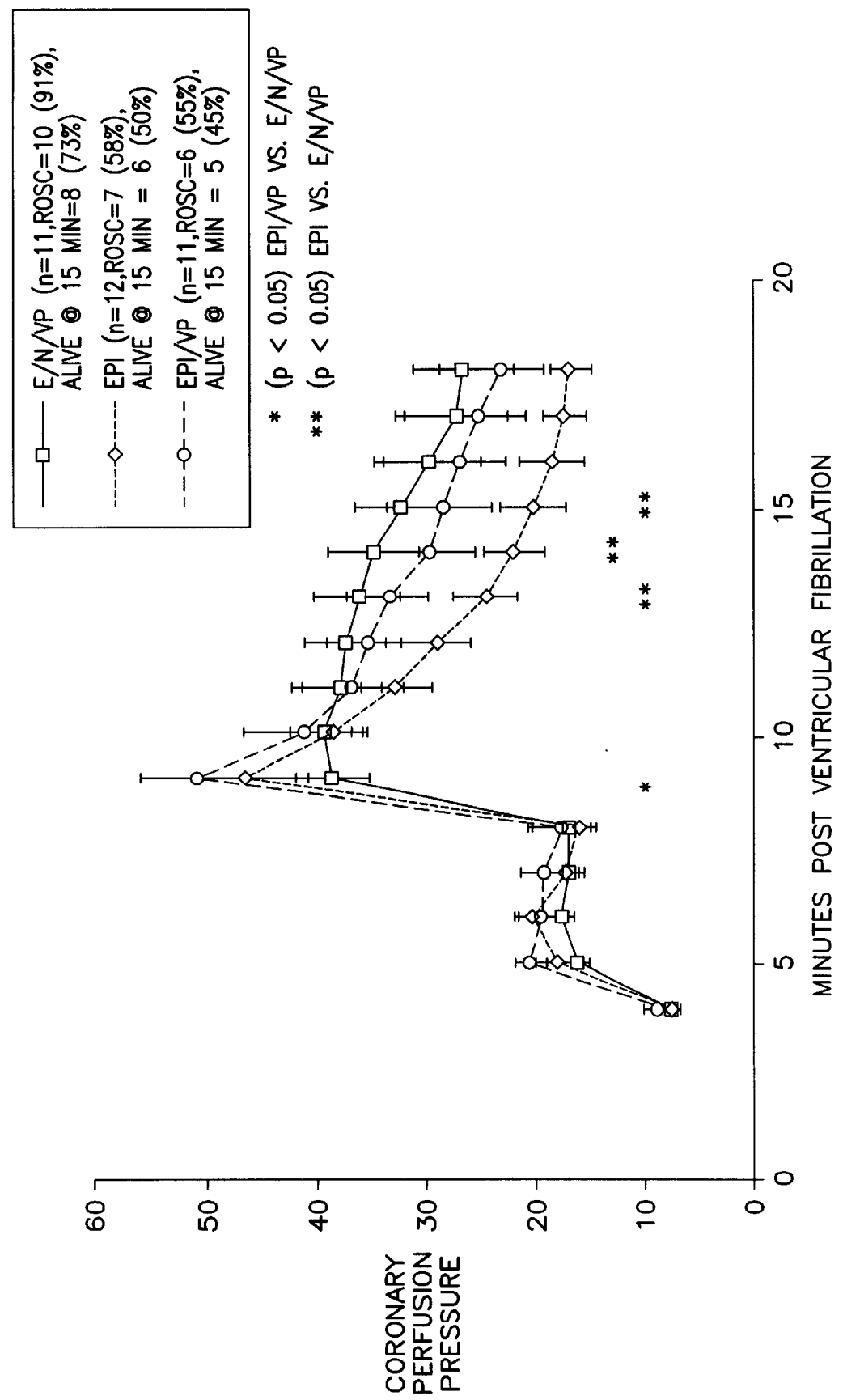
FIG. 4 illustrates the coronary perfusion pressures (CPP) (diastolic aortic minus right arterial pressures) of pigs (n>9 per group) resuscitated from ventricular fibrillation with epinephrine (EPI) alone 40 µg/kg; epinephrine 40 µg/kg and vasopressin (VP) 0.3 U/kg; and epinephrine 40 µg/kg and vasopressin (VP) 0.3 U/kg and nitroglycerine (N) 7.5 µg/kg.

The effect the direct nitric oxide donor DEA/NO, in combination with epinephrine and vasopressin was also studied in a porcine model of ventricular fibrillation as described above in Example 1. As shown in FIGS. 3 and 4, it was unexpectedly found that the combination of epinephrine 40 µg/kg, vasopressin 0.3 U/kg, and DEA/NO 0.14 µg/kg, also gives a marked and abrupt increase in coronary perfusion pressure, with peak diastolic coronary perfusion pressures again found to be as high or higher than those observed with the best "balanced" triple therapy of epinephrine (40 µg/kg), vasopressin (0.3 U/kg) and nitroglycerin (7.5 µg/kg).

Thus, the administration, during CPR, of a combination of L-arginine, nitric oxide, or a direct nitric oxide donor, and a vasopressor or a vasopressinergic agonist, can enhance the long term survival among certain cardiac arrest patients to a greater extent than the administration of other currently administered drugs or drug combinations.

All patents, patent documents and publications are incorporated by reference herein, as though individually incorporated by reference. While only certain preferred embodiments of this invention have been shown and described by way of illustration, many modifications will occur to those skilled in the art and it is, therefore, desired that it be understood that this is intended herein to cover all such modifications that fall within the spirit and scope of this invention.

What is claimed is:

1. A method for resuscitating a patient from cardiac arrest, comprising: (a) administering cardiopulmonary resuscitation ("CPR"), and (b) administering: i) an amount of one or more vasopressor agents, or one or more vasopressinergic agonists, or a combination thereof, sufficient to increase the patient's arterial blood pressure; and ii) an amount of L-arginine, nitric oxide, or a direct nitric oxide donor, or a combination thereof, sufficient to enhance arterial blood flow to the patient's brain and heart.

2. The method of claim 1 wherein one or more vasopressor agents are administered.

3. The method of claim 2 wherein the one or more vasopressor agents are selected from the group consisting of epinephrine, dopamine, norepinephrine, isoproterenol, phenylephrine, dobutamine, methoxamine, and mixtures thereof.

4. The method of claim 1 wherein an amount of epinephrine sufficient to increase the patient's arterial blood pressure is administered.

5. The method of claim 1 wherein an amount of vasopressin sufficient to increase the patient's arterial blood pressure is administered.

6. The method of claim 1 wherein an amount of a combination of epinephrine and vasopressin sufficient to increase the patient's arterial blood pressure is administered.

7. The method of claim 1 wherein L-arginine is administered.

8. The method of claim 1 wherein nitric oxide is administered.

9. The method of claim 1 wherein a direct nitric oxide donor is administered.

10. The method of claim 9 wherein the direct nitric oxide donor is DEA/NO, PAPA/NO, SPER/NO, DPTA/NO or DETA/NO; or a combination thereof.

11. The method of claim 10 wherein the direct nitric oxide donor is DEA/NO or PAPA/NO; or a combination thereof.

12. The method of claim 1 wherein an amount of epinephrine, sufficient to increase the patient's arterial blood pressure, and an amount of L-arginine, sufficient to enhance arterial blood flow to the patients brain and heart, are administered.

13. The method of claim 1 wherein an amount of epinephrine, sufficient to increase the patient's arterial blood pressure; and an amount of nitric oxide or a direct nitric oxide donor sufficient to enhance arterial blood flow to the patient's brain and heart, or a combination thereof, are administered.

14. The method of claim 12 wherein about 0.25 mg to 10 mg of epinephrine, and about 1 to 50 mg/kg of L-arginine are administered.

15. The method of claim 1 further comprising administering mannitol.

16. A kit for the treatment of cardiac arrest comprising packaging material containing: a) an amount of one or more vasopressor agents, or one or more vasopressinergic agonists, or a combination thereof, sufficient to increase a patient's arterial blood pressure; b) an amount of L-arginine, nitric oxide, or a direct nitric oxide donor, or a combination thereof, sufficient to enhance arterial blood flow to a patient's brain and heart; and c) instruction means indicating that the compounds described in a) and b) are to be administered to a patient undergoing cardiopulmonary resuscitation.

17. The kit of claim 16 wherein the packaging material contains an amount of L-arginine sufficient to enhance arterial blood flow to a patient's brain and heart.

18. The kit of claim 16 wherein the packaging material contains an amount of nitric oxide sufficient to enhance arterial blood flow to a patient's brain and heart.

19. The kit of claim 16 wherein the packaging material contains an amount of a direct nitric oxide donor sufficient to enhance arterial blood flow to a patient's brain and heart.

20. The kit of claim 16 wherein said packaging material further contains an amount of mannitol effective to inhibit edema when administered to a patient.

21. The kit of claim 16 wherein the packing material additionally includes one or more means for administering the compounds of a) or b).

22. A pharmaceutical composition comprising: a) an amount of one or more vasopressor agents, or one or more vasopressinergic agonists, or a combination thereof, sufficient to increase arterial blood pressure; b) an amount of L-arginine, nitric oxide, or a direct nitric oxide donor, or a combination thereof, sufficient to enhance arterial blood flow to the brain and heart; and c) a pharmaceutically acceptable carrier.

23. The composition of claim 22 comprising an amount of L-arginine sufficient to enhance arterial blood flow to the brain and heart.

24. The composition of claim 22 comprising an amount of nitric oxide sufficient to enhance arterial blood flow to the brain and heart.

25. The composition of claim 22 comprising an amount of a direct nitric oxide donor sufficient to enhance arterial blood flow to the brain and heart.

26. The pharmaceutical composition of claim 22 further comprising an amount of mannitol effective to inhibit edema.

27. A method for resuscitating a patient from cardiac arrest, comprising: (a) administering cardiopulmonary resuscitation ("CPR"), and (b) administering: I) an amount of one or more vasopressor agents, and one or more vasopressinergic agonists, sufficient to increase the patient's arterial blood pressure; and ii) an amount of L-arginine, nitric oxide, or a direct nitric oxide donor, or a combination thereof, sufficient to enhance arterial blood flow to the patient's brain and heart.

28. A method for resuscitating a patient from cardiac arrest, comprising: (a) administering cardiopulmonary resuscitation ("CPR"), and (b) administering: I) an amount of one or more vasopressinergic agonists sufficient to increase the patient's arterial blood pressure; and ii) an amount of L-arginine, nitric oxide, or a direct nitric oxide donor, or a combination thereof, sufficient to enhance arterial blood flow to the patient's brain and heart.

* * * * *

UNITED STATES PATENT AND TRADEMARK OFFICE
CERTIFICATE OF CORRECTION

PATENT NO. : 6,486,206 B1
DATED : November 26, 2002
INVENTOR(S) : Keith G. Lurie, M.D.

It is certified that error appears in the above-identified patent and that said Letters Patent is hereby corrected as shown below:

<u>Title page,</u>
Item [56], U.S. PATENT DOCUMENTS, delete "Pyzybelski" and insert
-- Przybelski -- therefor.

<u>Column 13,</u>
Line 9, delete "I)" and insert -- i) -- therefor.

<u>Column 14,</u>
Line 5, delete "I)" and insert -- i) -- therefor.

Signed and Sealed this

Fifth Day of August, 2003

JAMES E. ROGAN
*Director of the United States Patent and Trademark Office*